United States Patent [19]

Simmet et al.

[11] Patent Number: 5,505,716
[45] Date of Patent: Apr. 9, 1996

[54] EMBRYO COLLECTOR

[76] Inventors: Ludwig O. Simmet, 114 Shiloh Dr., Madison, Wis. 53705; Christian J. Simmet, Auberg 22, W-8311 Tiefenback, Germany

[21] Appl. No.: 12,226

[22] Filed: Feb. 2, 1993

[51] Int. Cl.$^6$ .......................... A61M 1/00; A61F 13/15; A61B 17/43
[52] U.S. Cl. .................. 604/318; 604/331; 600/34
[58] Field of Search ................... 128/760, 771; 604/36, 55, 317, 318–328, 330, 331, 332, 333, 334, 345, 355, 356, 406; 600/33, 34; 606/119, 121, 122, 123; 210/194, 299, 474, 477

[56] References Cited

U.S. PATENT DOCUMENTS

| | | | |
|---|---|---|---|
| 1,918,351 | 7/1933 | Schulze. | |
| 2,469,802 | 5/1949 | Voinovich | 210/122 |
| 2,879,207 | 3/1959 | Poitras | 195/139 |
| 3,769,171 | 10/1973 | Grimes et al. | 195/103.5 |
| 3,803,810 | 4/1974 | Rosenberg | 604/406 |
| 4,188,948 | 2/1980 | Swinton | 604/406 |
| 4,193,392 | 3/1980 | Barnett | 128/1 R |
| 4,275,732 | 6/1981 | Gereg | 128/276 |
| 4,516,973 | 5/1985 | Telang | 604/319 |
| 4,563,172 | 1/1986 | Ferguson | 604/55 |
| 4,781,706 | 11/1988 | Suzuki et al. | 604/317 |
| 4,817,599 | 4/1989 | Drews | 128/303 |
| 4,824,434 | 4/1989 | Seitz, Jr. | 604/27 |
| 4,912,037 | 3/1990 | Lemonnier | 435/34 |
| 5,042,979 | 8/1991 | Anderson et al. | 604/319 |
| 5,252,222 | 10/1993 | Matkovich et al. | 604/400 |

FOREIGN PATENT DOCUMENTS 4329965  11/1992  Japan ........................ 604/406

OTHER PUBLICATIONS

"BIOTECHNIK," MINITÜB GmbH, Germany.

*Primary Examiner*—Randall L. Green
*Assistant Examiner*—K. M. Reichle
*Attorney, Agent, or Firm*—Lathrop & Clark

[57] ABSTRACT

An embryo collection dish has a cylindrical sidewall with an inlet tube which communicates with an animal uterus from which the embryos are flushed. A lid is engaged with the dish and clamps a sheet of filter material therebetween. In use the filter is disposed vertically and the embryo cattier fluid is discharged from the device through an outlet tube which extends from the lid. The vertical distance between the inlet and outlet tubes is adjustable to control the volume of liquid retained in the dish along with the embryos. The dish together with its contents may be placed directly under a microscope for selection and extraction of the collected embryos. The device is sufficiently compact and fluid tight that it may be placed within a users clothing during collection to keep the embryos warm. Alternatively, an intermediate ring may be provided which joins a reusable lid to a disposable dish.

5 Claims, 7 Drawing Sheets

U.S. Patent    Apr. 9, 1996    5,505,716
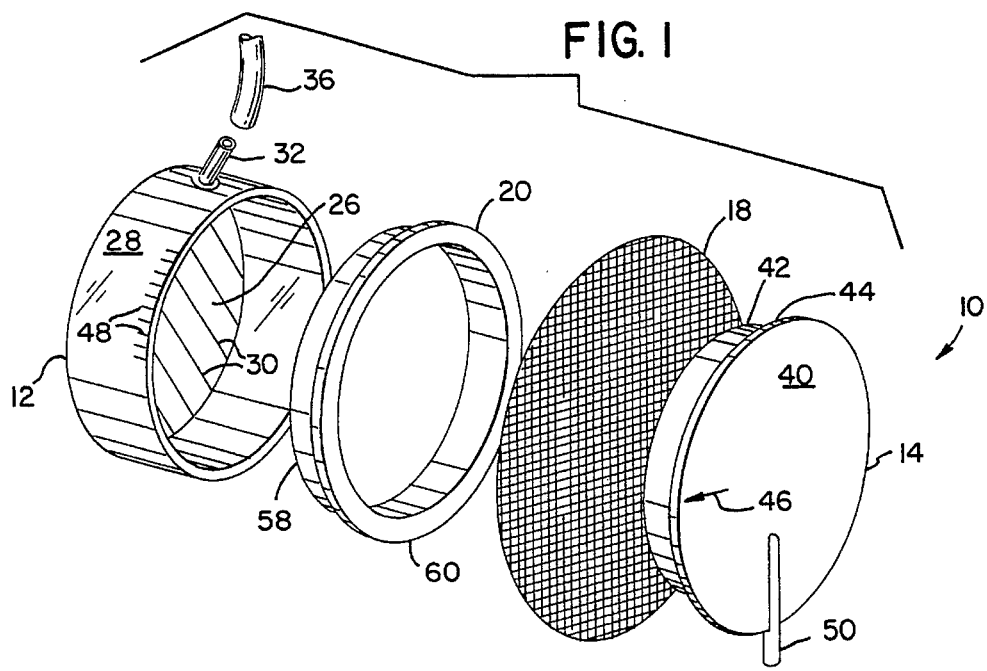
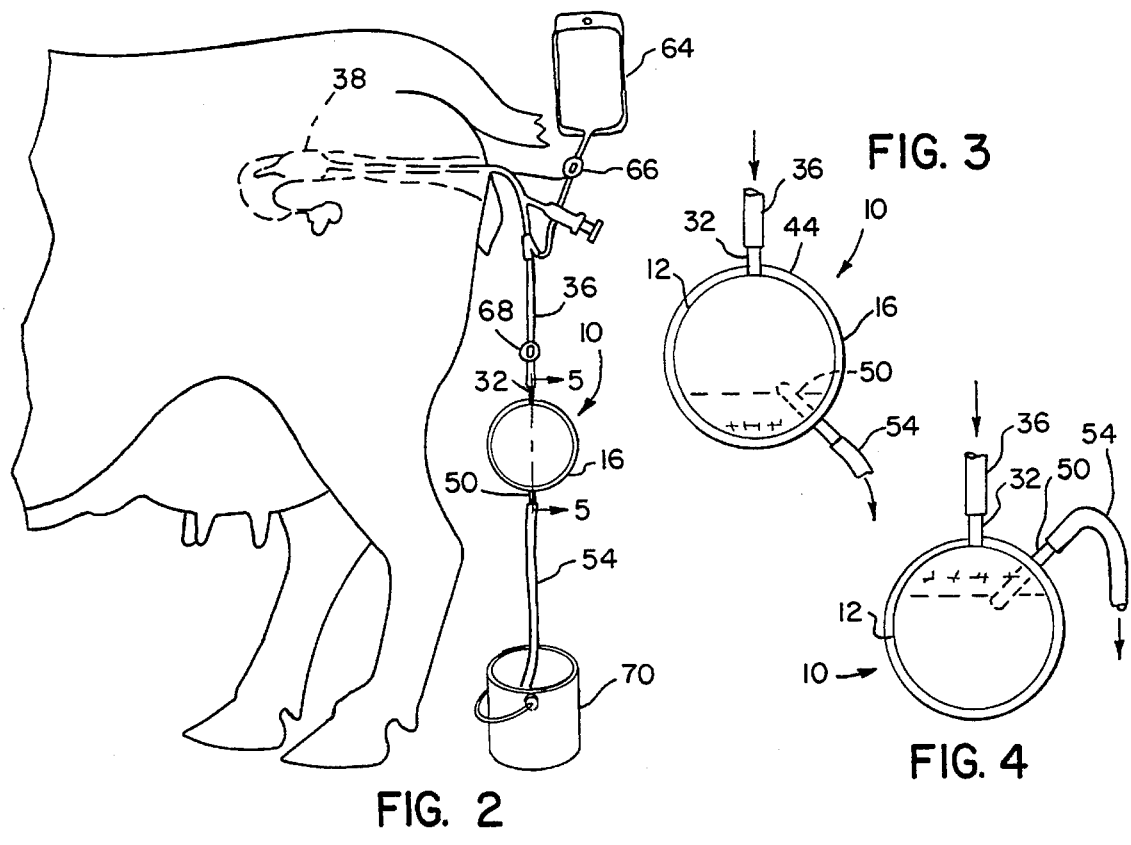

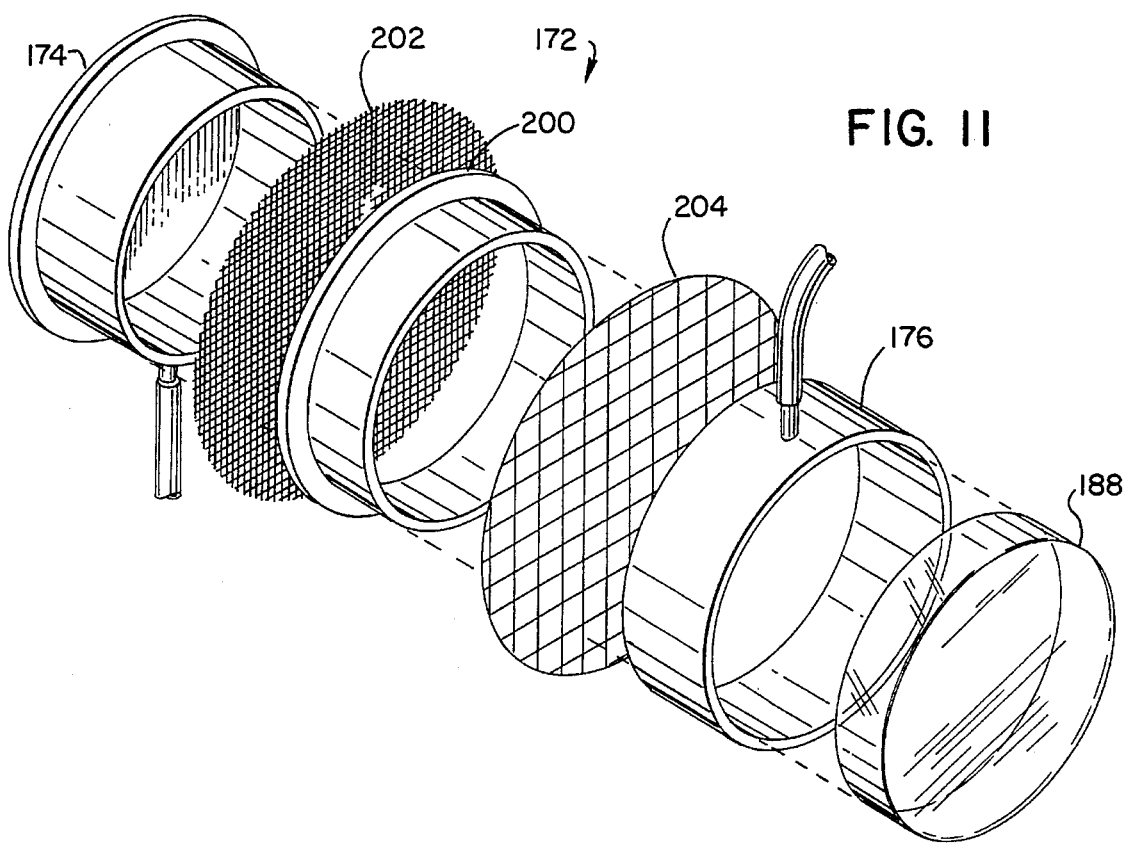
FIG. 11
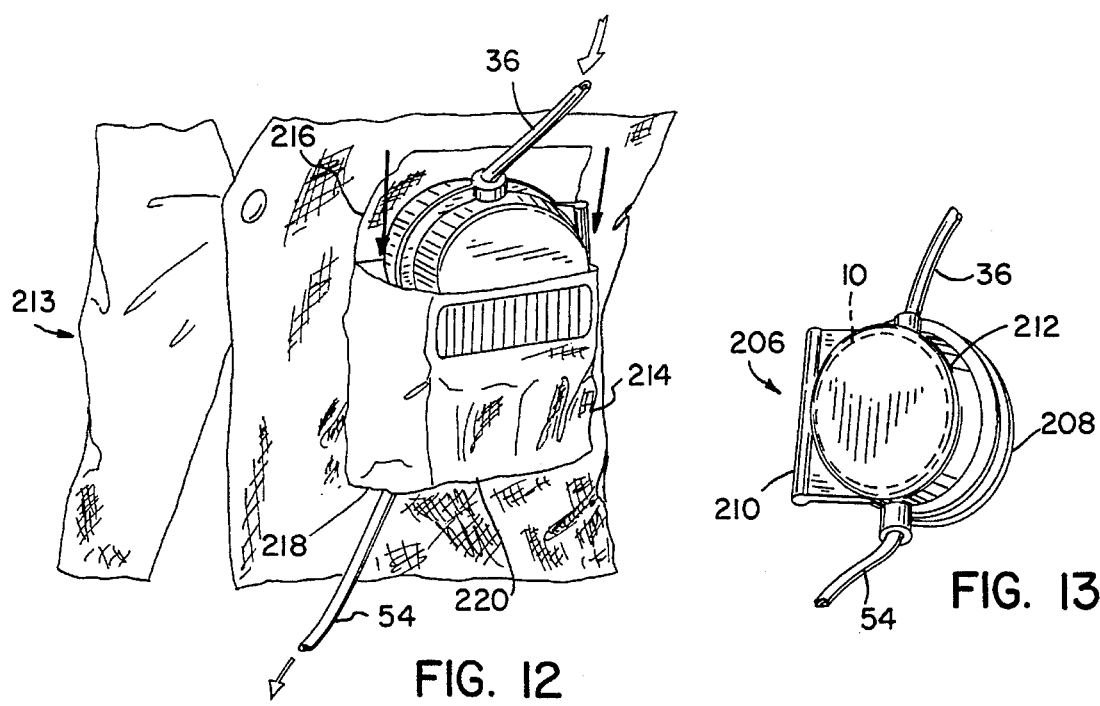
FIG. 12
FIG. 13

EMBRYO COLLECTOR

FIELD OF THE INVENTION

This invention relates to apparatus for facilitating animal reproduction in general and to apparatus for collecting and transporting the embryos of mammals in particular.

BACKGROUND OF THE INVENTION

For centuries selective breeding techniques have been employed to generate animal offspring having preferred qualities such as size, productivity and temperament. Male animals having desirable genetic characteristics may naturally sire offspring by multiple females in a single season. In recent times artificial insemination techniques have made possible the generation of thousands of offspring from a single parent at locations throughout the world. To adequately exploit the genetic material of female animals without requiring the female to give birth to all her offspring, a common practice is to inseminate the female by natural or artificial means and then extract the animal embryos at an age of three to five days. The extracted embryos are then typically frozen for shipment, processing, preservation or implantation at a later time.

It is well known in the art of animal husbandry to retrieve and collect mammalian embryos or ova from donor animals by flushing the animal's uterus with a solution and collecting the embryo bearing fluids, then passing the fluids through a filtration device in which the embryos are collected. Typical prior art devices require the collected embryos and solution to be transferred in the laboratory to a petri dish for examination beneath a microscope and removal and packaging of the embryos. Transfer of fluid from the collecting container to the petri dish is undesirable as embryos may be lost or damaged in the transfer. Some embryo collectors employ collection vessels which are transparent and which have a flat base to permit positioning on a microscope table, however these known devices are cumbersome and have filter openings formed in the vessel sidewall or base which are of limited extent and which may allow embryos to be trapped without liquid suspension. Furthermore, conventional adhesive attachment of filters across outlet openings leaves undesirable crevices in which embryos may become trapped. Frequently the collection of the animal embryos is performed on site in a barn. This subjects the embryos to the ambient temperature which may be lower than the temperature of the donor animal.

To maintain maximum embryo viability and health, it is desirable to keep the embryos at the approximate body temperature of the donor during the collection and transportation procedure since the collection alone may take one-half to one hour and may be performed in a barn in cold weather.

What is needed is a compact and easy to use embryo transfer and collection device which may be placed directly under a microscope for extraction of embryos, which efficiently separates the embryos from the carrier fluid without subjecting them to damage, and which is protected from contamination.

SUMMARY OF THE INVENTION

The animal embryo collector of this invention has a dish, a lid and a sheet of filter material interposed between the lid and the dish. The dish has a cylindrical sidewall which extends upwardly from a planar bottom which is adapted to be placed on a microscope stage for viewing and selecting the animal embryos. An inlet tube extends through the dish sidewall and opens into the dish to discharge a flushing solution containing embryos into the dish.

The lid has a top with downwardly extending sidewalls. The lid is engageable with the dish to form a fluid-tight compartment. An outlet tube extends out of the lid and is adapted to direct flushing solutions out of the lid. The outlet tube has a fluid outlet opening communicating with the interior of the lid.

A sheet of filter material is clamped between the dish and the lid. The filter has a pore size sufficient to prevent passage of an embryo from the dish while allowing the passing of flushing fluid into the lid. A retaining ring clamps the filter sheet to the lid. The dish engages with the lid beneath the retention fitting.

In use, the filter is positioned in a vertical orientation with the inlet tube oriented toward the donor animal. The inlet tube is attached to a balloon catheter which is placed in the animal's uterus. The flushing fluid volume is controlled in a conventional manner by valve feeding the balloon catheter.

The flushing fluid containing embryos enters into the dish through the inlet tube and passes across the filter into the lid. Embryos are collected in the dish with the waste fluids exiting through the outlet tube.

The positioning of the inlet opening of the outlet tube with respect to the lid sidewall permits the fluid volume retained within the device to be set at a desired level. Inlet and outlet tubes are positioned with respect to one another to determine a fluid collection volume within the device. At all times during the embryo collection procedure the embryos reside in a liquid volume.

To extract collected embryos the device is positioned horizontally and the lid and filter material removed. Embryos may then be located and extracted under a microscope.

It is an object of the present invention to provide an embryo collection device which permits the volume of fluid retained within the device to be set at a desired level.

It is also an object of the present invention to provide an embryo collection device which avoids damage to the embryos during collection.

It is another object of the present invention to provide an embryo collection device which will not leak during collection.

It is also an object of the present invention to provide an embryo collection device which may be positioned under a microscope for extraction of embryos without transfer to a separate vessel.

It is still a further object of the present invention to provide an embryo collection device which is sufficiently compact and leakproof to allow it to be held in an operator's pocket to keep the collected embryos warm.

It is yet another object of the present invention to provide an embryo collection device which is generally reusable and sterilizable.

Further objects, features, and advantages of the invention will be apparent from the following detailed description when taken in conjunction with the accompanying drawings.

BRIEF DESCRIPTION OF THE DRAWINGS

FIG. 1 is an exploded isometric view of the embryo collector of the present invention.

FIG. 2 is a front elevational view of the device of FIG. 1 shown in relation to a donor animal.

FIG. 3 is an enlarged front elevational view of the device of FIG. 2 illustrating the two halves rotated to increase the volume of liquid retained.

FIG. 4 is an enlarged front elevational view of the device of FIG. 3 illustrating the two halves rotated to retain a still greater volume of liquid.

FIG. 11 is an exploded isometric view of still another alternative embodiment of the embryo collector of the present invention.

FIG. 12 is a fragmentary perspective view of the device of FIG. 1 being inserted within the pocket of an insulating garment.

FIG. 13 is an isometric view of the device of FIG. 1 contained within a thermoformed clam shell package.

DESCRIPTION OF THE PREFERRED EMBODIMENT

Figure 5:
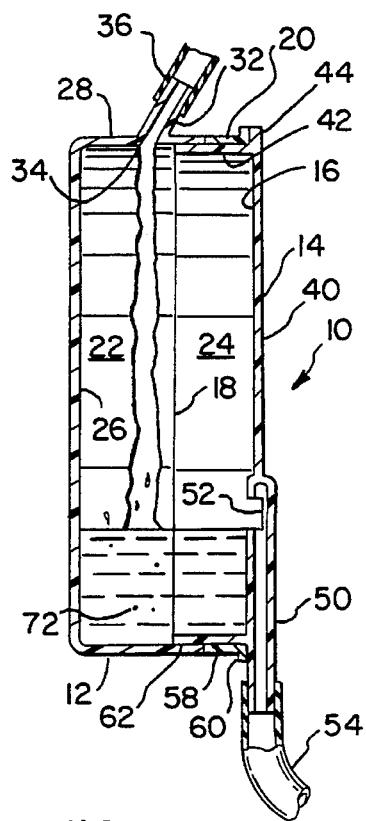
FIG. 5 is a cross-sectional view of the embryo transfer device of FIG. 2 taken along section line 5—5 showing the collection and filtration of embryo containing solutions during a collection procedure.

Referring more particularly to FIGS. 1–17 wherein like numbers refer to similar parts, an embryo collector 10 is shown in FIGS. 1–6. As best shown in FIG. 1, the device 10 has a transparent plastic embryo retaining dish 12 which engages with a plastic lid 14 to form a fluid tight filtration vessel 16. A sheet of filter material 18 is clamped between the dish 12 and the lid 14 and held in place by an annular plastic retaining ring 20. The filter material 18 divides the vessel 16 into two chambers: an inlet chamber 22 in which the embryos and a desired amount of solution are retained, and an outlet chamber 24 from which the solution escapes from the vessel 16.

Figure 8:
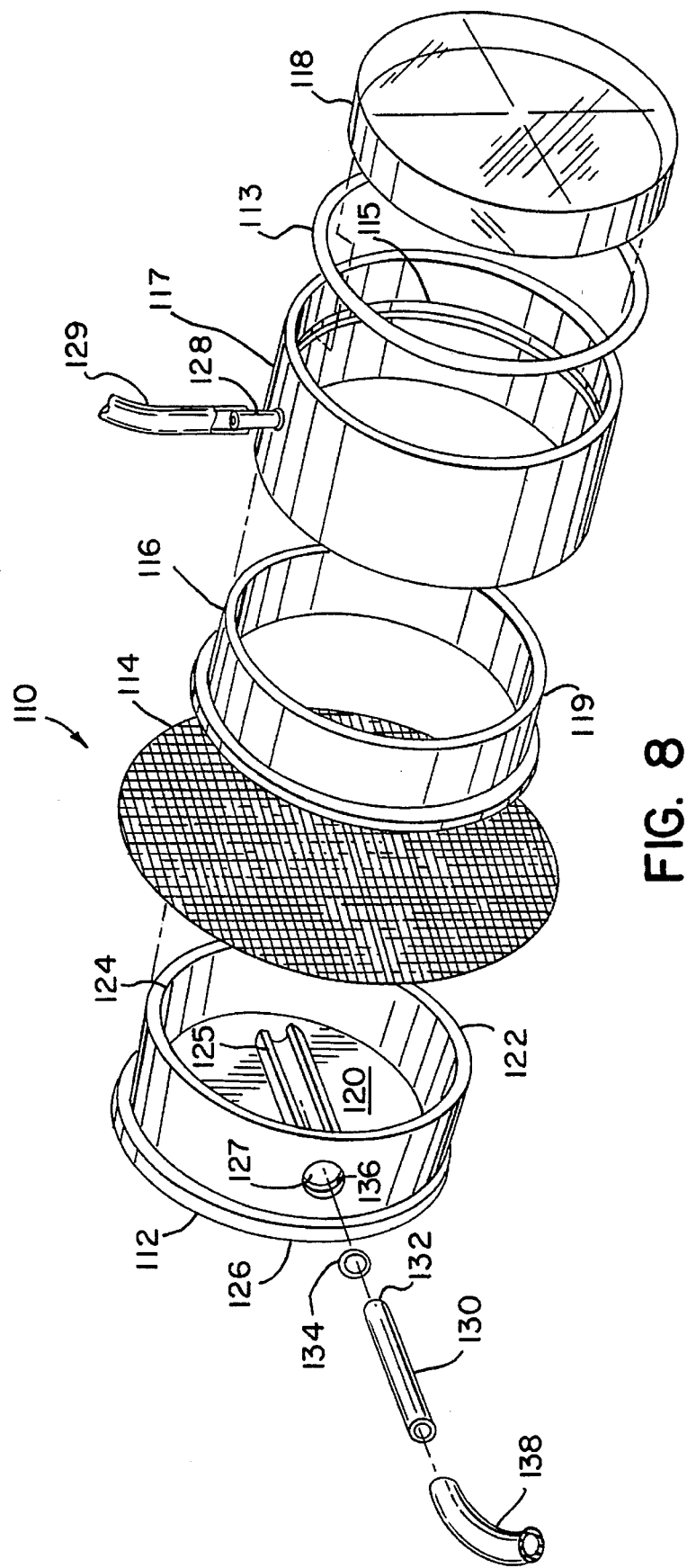
FIG. 8 is an exploded isometric view of an alternative embodiment embryo collector of this invention utilizing a disposable petri dish.

The dish 12 is substantially transpatent and has a planar circular bottom 26. A cylindrical sidewall 28 extends upwardly from the planar bottom 26. Grid markings are preferably formed in the dish bottom 26 which are visible under a microscope and which facilitate extraction of embryos from the dish 12. The grid markings 30 divide the dish bottom 26 into a number of linear regions, as shown in FIG. 1. Alternatively, the grid markings may define quadrant sectors as shown in FIG. 8, or may comprise any grid pattern.

An inlet tube 32 penetrates the dish sidewall 28. The inlet tube 32 discharges into the inlet chamber 22 of the vessel 16 through a fluid inlet opening 34. In a preferred embodiment the inlet tube 32 is integrally formed with the dish sidewall 28 and projects outwardly from the sidewall. The inlet tube is preferably angled from the bottom of the dish.

Flexible tubing 36 connects the inlet tube 32 to a balloon catheter flushing device 38 described more fully below.

The lid 14 has a circular top 40 and a cylindrical downwardly extending sidewall 42 which generally defines the outlet chamber 24. A lip 44 projects outwardly from the top 40 perpendicular to the sidewall 42. The lip 44 is somewhat thicker than the top 40.

Indicia 46, for example in the shape of an arrow, are incorporated onto the exterior of the lid top 44. The indicia 46 cooperate with graduated markings 48 on the dish sidewall 28 to aid in setting the volume of liquid retained within the vessel 16 as described more fully below. Alternatively the protruding outlet tube 50 may substitute for the lid indicia to gauge vessel retained volume.

An outlet tube 50 extends through the lid sidewall 42 out of the lid and directs flushing fluid out of the device I0. The outlet tube 50 has cylindrical walls preferably integrally formed with the lid 14. The outlet tube 50 has an outlet opening 52 within the lid which is spaced a sufficient distance from the lid sidewall 42 to ensure proper fluid retention within the vessel 16 to ensure hydralion of the collected embryos. In the preferred embodiment the outlet tube is a rigid plastic part formed integrally with the lid top 40 and the outlet opening 52 is an aperture formed in the tube and spaced from the lid sidewall 42. The outlet tube 50 is adapted to snugly receive a length of flexible tubing 54 which drains away excess solution.

The filter material 18 is preferably circular, and is sufficiently larger in diameter than the lid sidewall to effectively cover the opening in the lid defined by the lid sidewall 42. The pore-size of the filter material 18 is sufficient to prevent an embryo from passing through the filter while allowing flushing fluids and other biological substances to pass through. For example, a 40 micron filter pore size may be used for collection of cattle embryos.

The filter material 18 is clamped against the lid 14 by a retention fitting or retaining ring 20. The retaining ring 20 is preferably a molded plastic part which has a ring sidewall 58 which engages the filter material between the ring sidewall and the lid sidewall 42. A flange 60 projects outwardly from the ring above the sidewall 58. In assembling the device 10 the ring 20 is fit over the filter material 18 which is laid over the lid sidewall and pressed into place such that the retaining ring flange 60 abuts the lid lip 44 forming a fluid tight seal between the lid, filter and the ring. The inner diameter of the ring 20 is only slightly greater than the outer diameter of the lid sidewall 42 such that the filter material 18 holds the ring engaged with the lid 14 in a friction fit. The height of the ring sidewall 58 is less than the height of the lid sidewall 42 such that an axially extending portion 62 of the filter material is exposed beneath the retaining ring 20. This portion 62 engages with the dish sidewall 28 to hold the dish together with the lid 14 in a tight but releasable friction fit. The dish is thus engaged with the lid 14 in a fluid tight seal.

Although the device 10 will preferably be supplied with the filter material in place, it may be supplied unassembled so the end user may utilize filter material suited to a particular application.

When it is desired to collect embryos from a subject animal, as shown in FIG. 2, the flexible inlet tubing 36 is connected to a balloon catheter 38 which has been inserted in a conventional manner into the uterus of the subject, such as a cow or a horse. Conventional embryo flushing techniques are then performed. A flushing fluid of sterile solution is released from an elevated reservoir 64 and is introduced through the balloon catheter 38 into the animal's uterus. The uterus is washed with a quantity of fluid sufficient to suspend the embryos. Typically one to two liters (1) of a flushing solution are used to flush a cow's uterus. The cow's uterus holds no more than 50 to 60 milliliters (ml) of fluid. In a process which may last thirty to sixty minutes, small quantities of flushing fluid are repeatedly introduced into the subject's uterus. Once the uterus is filled, a clamp 66 or valve in the supply line of fluid from the reservoir 64 is closed and a second clamp 68 or valve in the inlet tubing 36 is opened to allow the flushing fluid and any suspended embryos to discharge from the uterus into the filtration vessel 16 of the device 10.

As best shown in FIG. 5, the device 10 is suspended from the flexible inlet tubing 36 in a generally vertical orientation. Fluid enters the vessel 16 through the inlet opening 34 and flows across the filter material 18 from the inlet chamber 22 to the outlet chamber 24 and thence through the outlet tube 50 into the outlet flexible tubing 54 which discharges the waste fluid into a waste receptacle such as a bucket 70. The mammalian embryos 72, which are too large to pass through the filter material 18, are retained within the inlet chamber 22.

The generally vertical orientation of the filter material 18 has several beneficial effects. First, the flow of liquid across the filter material is generally horizontal, and thus not beneath the total level of fluid contained within the vessel, subjecting the suspended embryos to reduced pressure levels. Secondly, as the flow through the device 10 is intermittent as a result of the repeated filling and flushing of the subject animal's uterus, the flow into the vessel will at times be intense, and at other times relaxed. The vertical filter orientation presents a greater surface area of filter material to the liquid as the volume of liquid within the vessel increases. This greater surface area which is presented as the fluid level ascends results in a reduced fluid flow rate across the filter and again reduced forces exerted on the fragile embryos. Furthermore, the denser mucus will tend to sink towards the dish sidewall, not onto the filter.

The vertical orientation of the filter in use also has protective benefits to the embryos being collected. Should the device 10 be jarred tilted or displaced so as to tip the vessel and elevate the outlet opening above the inlet opening, at worst a greater quantity of flushing fluid than desired will be temporarily retained within the vessel. At no time will the embryos be left without sufficient liquid to support them and prevent their desiccation and death. In any event, at the time of completion of the collection the device 10 may be returned to its proper orientation without damage to the collected specimens.

When the device 10 is disassembled for extraction of embryos, the retaining ting will hold the filter material in place over the lid, allowing embryos which may have become attached to the filter to be flushed off the filter, either by flowing liquid in through the outlet tube, or by simply applying water to the exposed filter material.

As all the waste fluid is discharged through the outlet tubing 54 at a location remote from the device 10, the exterior of the device and the surrounding area remains unsoiled by flushing solution. This feature of the device 10 permits the device to be placed close to the warmth of an operator's body during the collection process, for example within a pocket beneath a jacket or coat. In this way the embryos may be protected against debilitating cold during collection.

The cleanliness of the device 10 may further be protected in the unsanitary conditions of most collection sites by packaging the device in plastic shrinkwrap or a thermoformed clam shell package 206, shown in FIGS. 12 and 13, with only the inlet flexible tubing 36 and the outlet flexible tubing 54 extending from the package. The thermoformed package has a base 208 attached by an integral hinge 210 to a cover 212. The packaging serves to prevent dust, soil, animal wastes and other debris from accumulating on the dish 12 during collection and hence preserves the optical clarity of the dish under microscopic inspection. The shrinkwrap may be of an opaque plastic to protect the device's contents from exposure to damaging ultraviolet light.

As shown in FIG. 12, the user of the device 10 may employ a specialized garment with an exterior pocket 214 with an upwardly opening flap 216 which allows the device 10 to be inserted into the pocket. The pocket will preferably have a lower exit hole 218 for the passage of the flexible outlet tubing 54. The garment 213 preferably has an inner layer adjacent the wearer's body that is relatively thin and conducive to heat transfer, and an outer layer 220 which is thermally insulated to retain the heat of the wearer's body and to thus warm the contents of the device 10.

The lid 14 and dish 12, although firmly connected, are rotatably positionable. Thus, if desired, the volume of fluid retained within the vessel 16 may be adjusted by changing the vertical separation between the inlet opening 34 and the outlet opening 52. The indicia 46 and base markings 48 facilitate setting the volume at a desired level. As shown in FIGS. 3, 4 and 5, the smallest volume of fluid contained in the device will occur when the outlet opening is positioned at 180° degrees from the inlet opening. The maximum volume will occur when the outlet opening is positioned at 0° degrees from the inlet opening. The fluid outlet opening, because it is spaced radially inwardly from the lid sidewall, when rotated tracks in a concentric circle with a smaller circumference than the circumference of the dish. This concentricity provides the variable volume feature of the device. The other factor in the volume determination is the spacing of the fluid inlet opening from the sidewall.

For embryo collection and transport devices of the present invention which do not have cylindrical walled dishes and lids, the dish may be provided with a plurality of outlet tubes, each having an outlet opening within the dish which is spaced a greater distance from the sidewall. To select the amount of liquid retained with this device, a user would plug the outlets not used and connect the flexible outlet tubing to the outlet tube having an opening at the desired level.

An exemplary dish is approximately 8 cm. in diameter and approximately 2 cm. tall. The entire device 10 is approximately 3½ cm. high by 8 cm. providing a total volume of approximately 180 milliliters.

Figure 6:
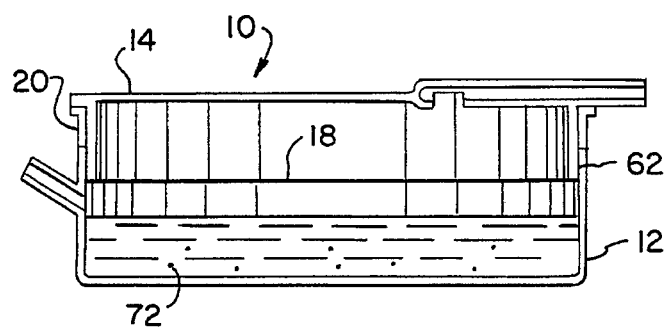
FIG. 6 is a cross sectional view of the embryo collector of FIG. 5 showing the device in a horizontal orientation preparatory to viewing under a microscope.
Figure 7:
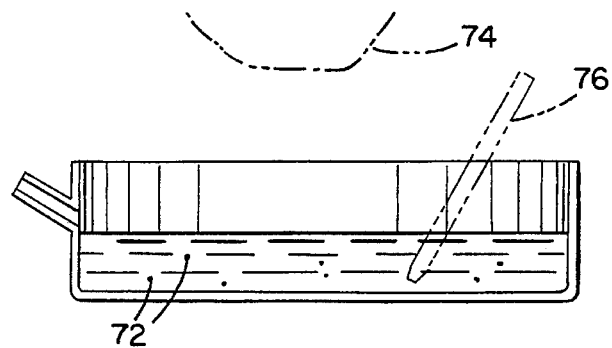
FIG. 7 is a cross sectional view of the dish portion of the device of FIG. 6 on a microscope viewing stand, with the collection probe and the microscope objective shown in phantom.

After the collection procedure has been completed, the inlet and outlet flexible lengths of tubing are clamped or tied off and the fluid tight assembly is transferred to a laboratory for extraction of the collected embryos. When the dish is placed on a horizontal surface, as shown in FIG. 6, all the solution and embryos within the vessel 16 will collect within the dish 12. The outlet opening 52 is spaced sufficiently from the lid sidewall 42 that enough solution is retained within the dish to sufficiently wet the collected embryos and prevent dehydration and death of the embryos. However, it is important that an excessive amount of liquid not be retained, for in that case the fluid level would exceed the height of the dish sidewall 28 and would overflow from the dish when the lid 14 was removed. The volume retained within the vessel is also best set at a low level to make extraction of embryos less difficult. Once in the laboratory the lid and filter material 18 are removed from the dish 12. If material is clinging to the filter material, sterile fluid may be injected into the lid 14 through the outlet tube 50 and any embryos which remain attached to the filter material may be backwashed into a separate petri dish for later examination and extraction. As best shown in FIG. 7, the dish 12 is placed on the stage of a stereomicroscope beneath the objective 74. A selection probe or pipette 76 may then be used to extract and package for shipment those embryos identified through the stereomicroscope.

The device may be fabricated of disposable plastic, or alternatively may be molded of materials which are sterilizable and which do not produce chemicals which harm embryos. The device 10 may be made entirely of transparent material to facilitate inspection of the interior. The dish bottom is transparent in order to permit direct use under the stereomicroscope.

Figure 9:
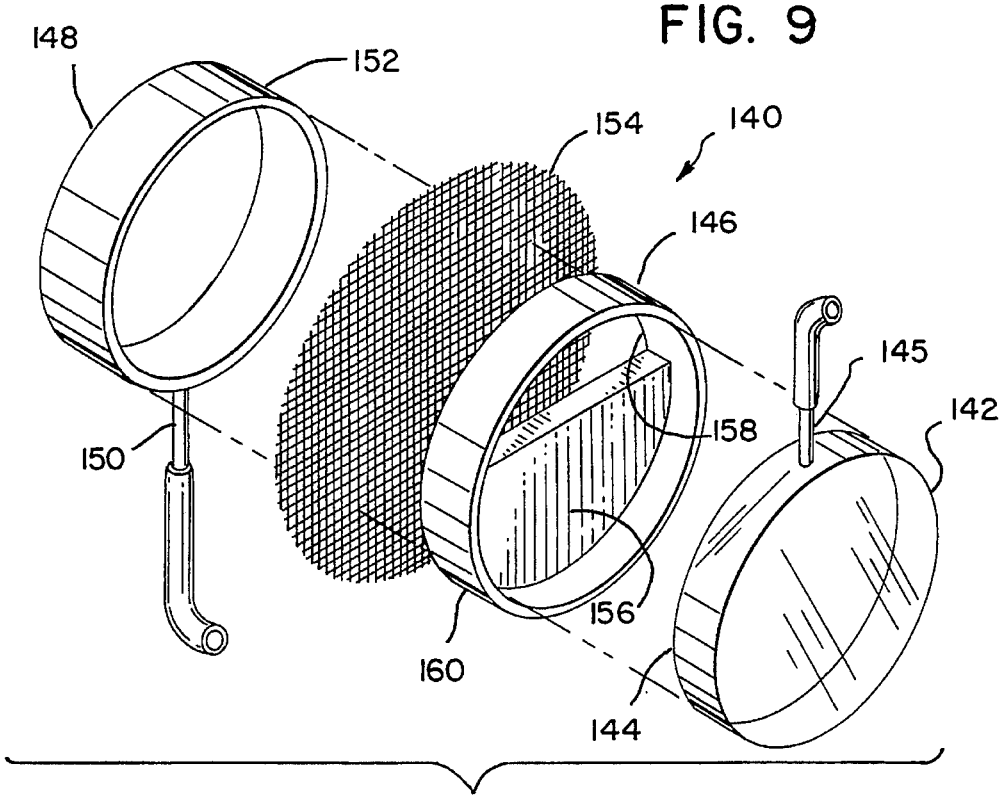
FIG. 9 is an exploded isometric view of another alternative embodiment embryo collector of this invention.

An alternative reusable embryo collector 110, shown in FIGS. 8 and 9, has a lid 112, a filter 114, and a retaining ring 116 which engage in a friction fit with a stainless steel or heat resistant plastic sleeve 117. An o-ring 113 fits within a gland in the sleeve and releasably engages with a conventional petri dish 118.

The lid 112 has a circular top 120 with a cylindrical sidewall 122 extending upwardly from the top 120. A lid lip 126 projects outwardly from the lid base 120 approximately perpendicular to the lid sidewalls 122.

The lid sidewall 122 has an opening 127 communicating with the lid cavity 124 defined by the sidewalls 122 and the lid top 120. A c-shaped channel 125 is formed within the lid cavity on the underside of the lid top 120. The channel 125 runs from the lid sidewall opening 127 across a substantial portion of the lid width. A rigid outlet tube 130 is inserted through the opening 127 and is slidable within the channel 125 to position the outlet opening 132 of the outlet tube 130 at a desired position within the lid 112. An o-ring 134 is positioned in a gland 136 within the lid sidewall opening 127 to form a liquid tight seal with the outlet tube 130. A flexible outlet tubing 138 is connected to the outlet tube 130 to direct waste fluid to an appropriate receptacle. It should be noted that the lid 112 and positionable outlet tube may also be employed with the device 10 if desired.

The filter 114 is of a circumference sufficient to cover the lid top 120 and the lid sidewall 122 and is positioned across the lid cavity 124. The filter 114 has a pore size sufficient to prevent an embryo from passing through the filter while allowing flushing fluids and mucus to pass through.

The retaining ring 116 has ring sidewalls 119. The retaining ring 116 fits over the lid sidewall 122 with the filter 114 therebetween.

The cylindrical sleeve 117 has portions defining an inlet tube 128 which extends into the sleeve. The sleeve inlet tube directs flushing fluid containing embryos into the sleeve interior. A flexible inlet tube 129 is connected to the inlet tube 128 to conduct fluid from the balloon catheter. An o-ring gland 115 is an internal groove formed on the interior surface of the sleeve 117.

A resilient o-ring 113 is positioned within the o-ring gland 115 to releasably engage a conventional laboratory container such as a disposable petri dish 118 in a fluid tight seal. The o-ring 117 is seated in a position spaced from the ends of the sleeve.

For convenience the device 110 may be used, sterilized and reused with a new petri dish. The device 110 may then be economically used with a variety of readily available petri dishes of different capacities and designs.

A second alternative embodiment of the embryo collector of the present invention is shown in FIG. 9. The device 140 has a transparent dish 142 having a base and an upwardly extending sidewall 144 through which an inlet tube 145 discharges. An annular plastic sleeve 146 connects the dish 142 to a lid 148 having a fluid outlet robe 150. The lid has a cylindrical sidewall 152. The inner diameter of the sleeve 146 is sufficient to provide an interference fit with the dish 142. A filter material sheet 154 is clamped between the lid 148 and the sleeve 146. A liquid impervious barrier 156 is integrally formed with the sleeve 146 and blocks the passage of liquid between the dish 142 and the lid 148 except through the sector shaped opening 158 defined within the sleeve sidewall 160 and above the barrier 156.

The level of the opening 158 determines the amount of liquid which will be retained within the device 140. Rotation of the sleeve 146 may thus control the desired level of retained liquid.

The device 140 is employed in a manner generally similar to the device 10. The device 140 may advantageously be produced at low cost as the dish 142 and lid 148 may be formed as identical pieces utilizing the same molds.

To securely engage the sleeve 146 with both the lid and the dish the interior diameter of the sleeve may be formed somewhat larger on the side which mates with the dish. Alternatively a constant internal diameter sleeve may be provided with a second filter sheet between the sleeve and the dish.

Figure 10:
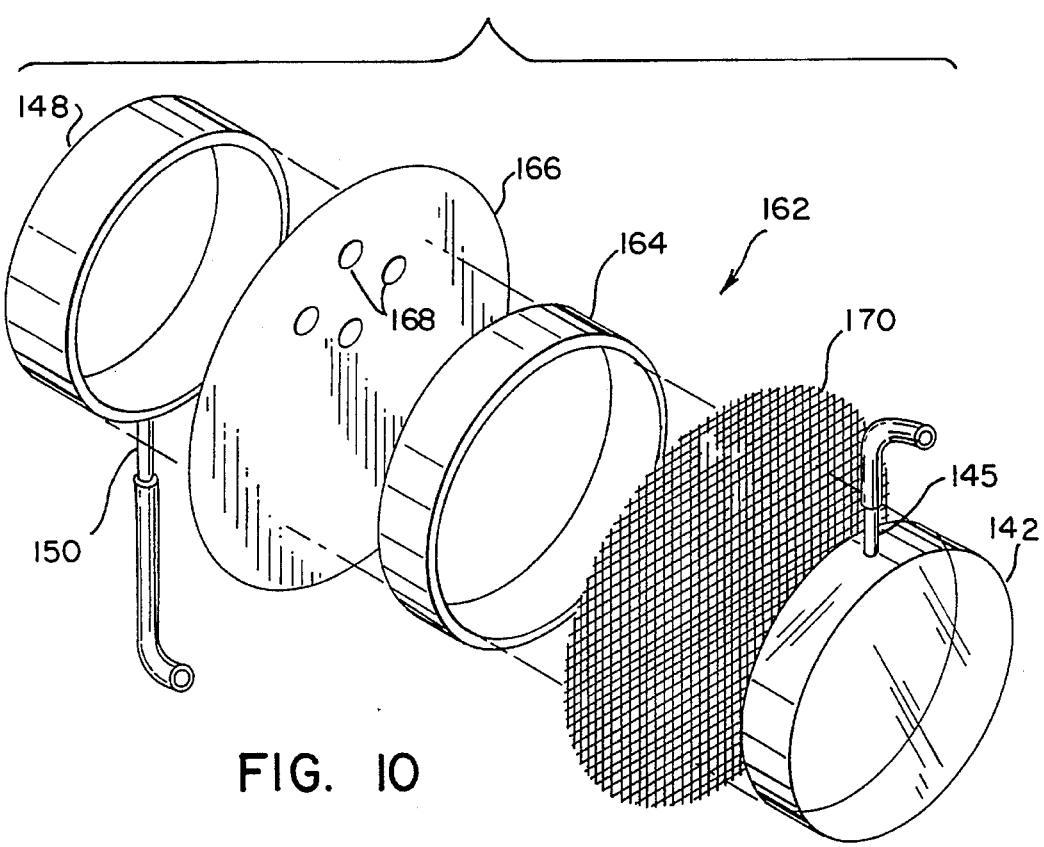
FIG. 10 is an exploded isometric view of yet another alternative embodiment embryo collector of this invention.

A third embodiment of the embryo collector of the present invention is shown in FIG. 10. The device 162 has a dish 142 and lid 148 identical to those of the dish 142. The dish and lid are joined by a sleeve 164 which is a simple annulus which may be conveniently and economically formed such as by extrusion. A fluid impervious flexible sheet barrier 166 is engaged between the lid 148 and the sleeve 164 in a liquid tight friction fit. The barrier 166 has holes 168 punched or die cut therein for the flow of fluid therethrough. A filter material sheet 170 is engaged in a friction fit between the dish 142 and the sleeve 164. The orientation of the holes 168 in the barrier sheet 166 will determine the liquid level retained within the device 162.

In certain applications it may be desirable to provide the embryo collection and transport device of the present invention with two or more filters to prevent mucus and other larger particles plugging or clogging the small pore filter 202. The device 172 shown in FIG. 11 has a reusable lid 174 and sleeve 176 for use with a disposable petri dish 188. A retaining ring 200 fits over a small pore filter 202 and the lid 174 to stretch the filter over the lid. The sleeve 176 fits over the retaining ring 200 and clamps a coarse filter 204 therebetween. The sleeve is sized to engage with the petri dish 188 in a friction fit. The coarse filter 204 is formed of a sheet of filter material which permits the passage of particles which are larger than those permitted to pass though the small pore filter 202.

Figure 14:
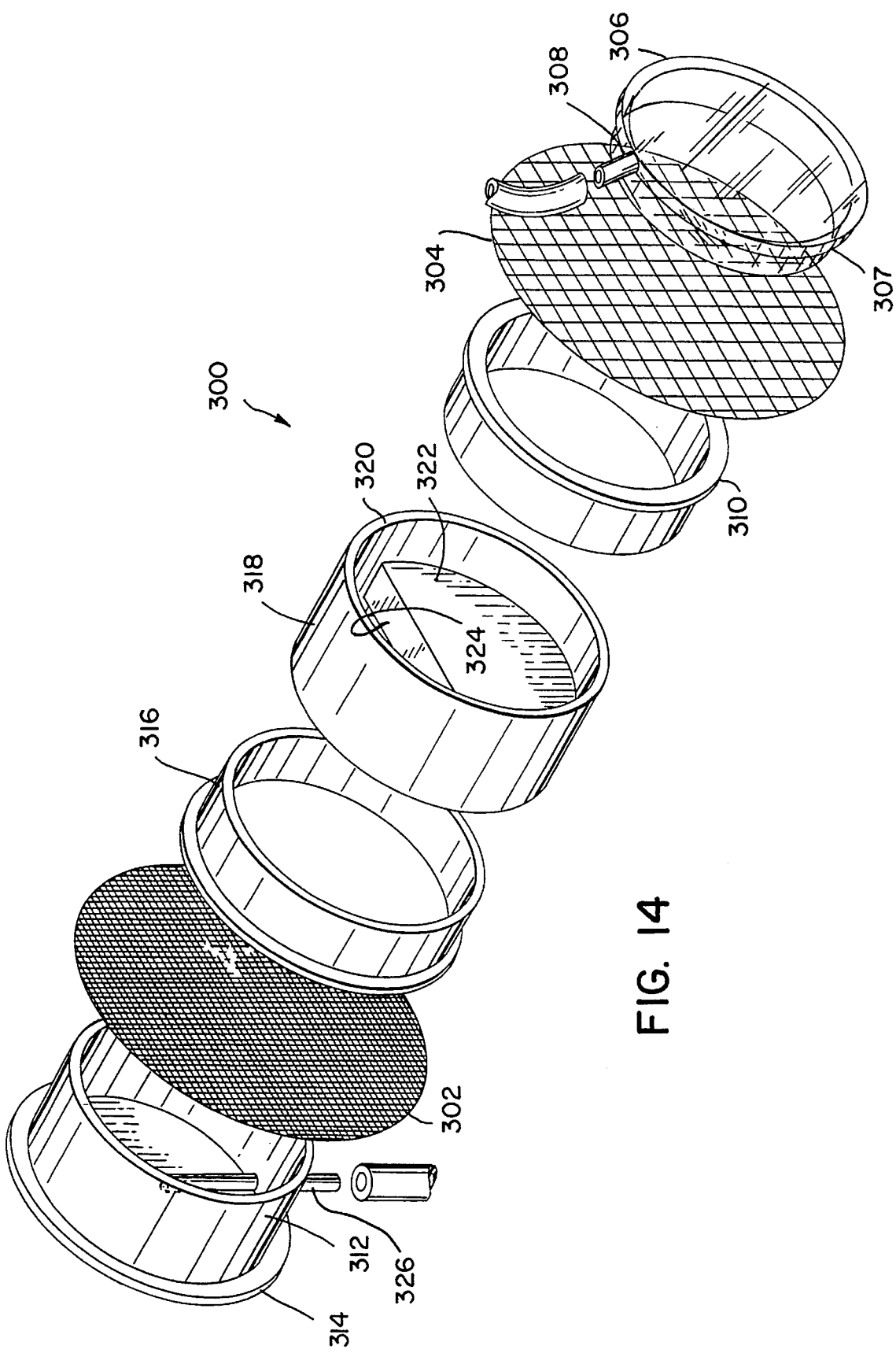
FIG. 14 is an exploded isometric view of an alternative embodiment of the collector of the present invention having a compartmented sleeve for retaining fluid from which mucus has been filtered out.

Another embodiment of the embryo collector of the present invention is shown in FIGS. 14–17. The collector 300 is advantageously employed to separate out a portion of the mucus retained in the collector. The collector 300 has a small pore filter 302 through which embryos may not pass and a large pore filter 304 which is sized to prevent the passage of mucus therethrough. The collector 300, as best shown in FIG. 14 has a transparent dish 306 with an upwardly extending sidewall 307 through which an inlet tube 308 extends. The large pore filter 304 is placed over the dish sidewall 307, and a first retaining ring 310 is pressed over the filter to hold it in place. In a similar manner the small pore filter 302 is held in place over the sidewall 312 of the lid 314 by a second retaining ring 316.

Figure 17:
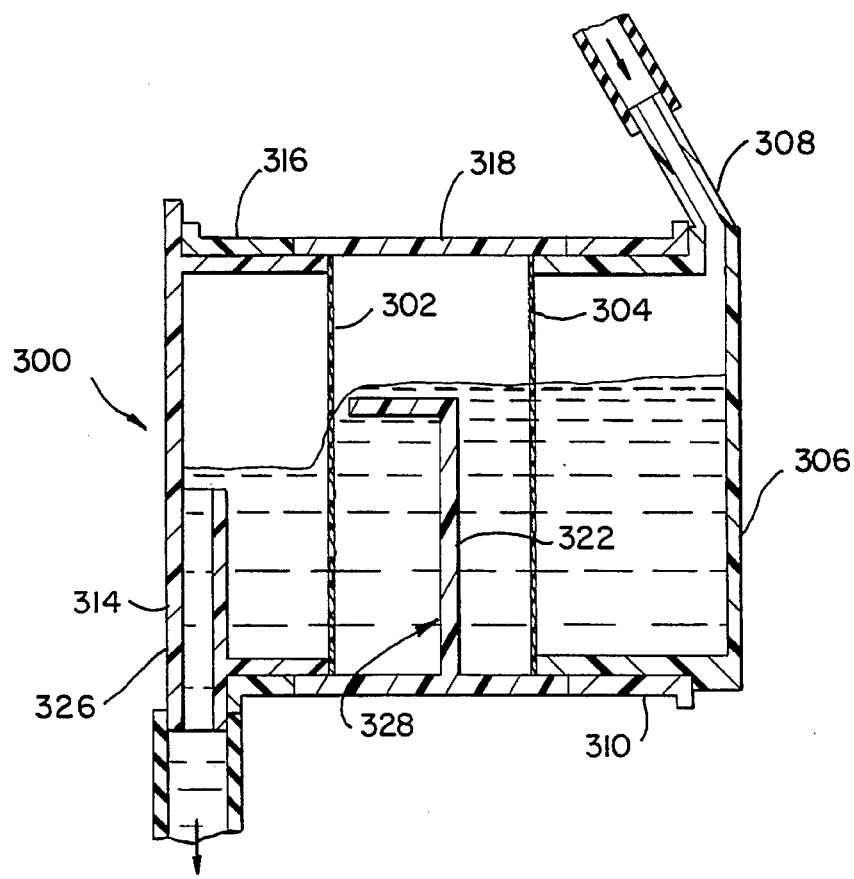
FIG. 17 is a cross-sectional view of the collector of FIG. 14 in the process of filtering an embryo and mucus containing fluid.
Figure 15:
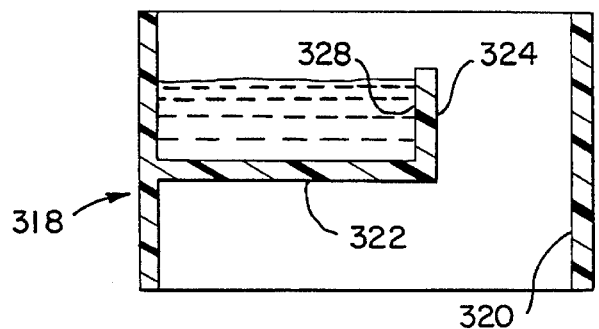
FIG. 15 is a cross-sectional view or the compartmented sleeve of the collector of FIG. 13 with liquid retained therein.

A transparent plastic sleeve 318 fits over the filter covered sidewalls 307, 312 of the dish 306 and lid 314. The sleeve 318 serves to connect dish and the lid while separating the large pore filter from the small pore filter as shown in FIG. 17. However, as shown in FIG. 15, the sleeve also serves as a second collection and examination dish.

The sleeve 318 has a cylindrical sidewall with an impervious plastic barrier 322 which extends within the sidewall to a desired height, preferably greater than one half the height of the sleeve 318. The barrier 322 has a lip 324 which extends perpendicular to the barrier towards the lid.

As shown in FIG. 17, during collection fluid containing embryos and mucus flows into the dish 306. Fluid containing embryos flows across the large pore filter 304 into the sleeve 318, mucus is retained within the dish 306. The embryo containing fluid flows over the barrier lip 324, through the small pore filter 302, into the lid 314 and out of the collector through the outlet tube 326.

Once collection has been completed the inlet and outlet tubes are sealed. While still in its vertical orientation the collector 300 divides its contents into three regions: fluid, mucus and perhaps embryos remain within the dish 306; fluid and embryos remain within the sleeve 318, and fluid only remains within the lid 314.

Figure 16:
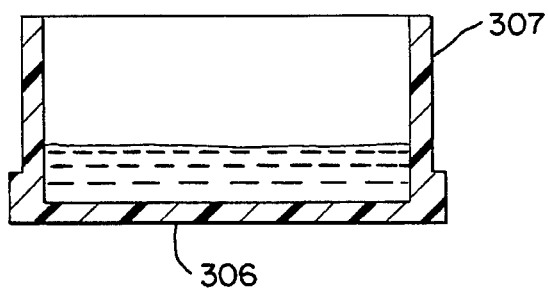
FIG. 16 is a cross-sectional view of the dish of the collector of FIG. 14.

As shown in FIGS. 15 and 16, after collection the collector 300 is rotated 90 degrees and placed so that the dish 306 rests on a horizontal surface. First the lid 314 and the attached small pore filter and ring 310 are removed from the sleeve 318. Any embryos remaining on the small pore filter may be flushed into a separate petri dish if desired. At this point liquid will have collected both within the compartment 328 defined by the barrier 322, the lip 324 and the sleeve sidewall 320, and also in the dish 306. The fluid contained within the compartment 328 will be free of mucus and will be easily examined for extraction of embryos. The fluid within the dish 306 will contain mucus, and may contain some embryos also. It may be handled in the way described above with respect to the collector 10.

It is understood that the lids, rings, and sleeves of the device may be made of autoclavable or sterilizable material such as glass, metal such as stainless steel, or heat resistant plastics. The dish may be made of glass or transparent plastic.

It is important to note that where embryos have been referred to herein, other biological reproductive products are also meant to be included, in particular unfertilized ova. The various embodiments of the invention disclosed above may, with substitution of appropriate filter material to accommodate the sizes of biological product to be obtained, be used for collecting of these other products.

It should be noted that a device may be formed in which the filter material is fixedly connected to the lid such as by welding or adhesive attachment. Such an embodiment of the invention would not require a retaining ring to hold the material in place.

It is understood that the invention is not confined to the particular construction and arrangement of parts herein illustrated and described, but embraces such modified forms thereof as come within the scope of the following claims.

It should be noted that the dish and lid of the present invention may be formed of any desired mating shape in addition to the cylindrical shapes disclosed above. Furthermore the dish and lid shape may be any desired regular polygon to permit adjustment of position of inlet and outlet openings in incremental steps.

We claim:

1. A device for collecting animal embryos suspended in a flushing solution, the device comprising:

a. a dish having a bottom and an upwardly extending dish sidewall, wherein an unobstructed volume is defined within the dish sidewall;

b. an inlet tube extending into the dish sidewall and adapted to direct the flushing solution containing the embryos into the dish;

c. a lid having a top and a downwardly extending sidewall, wherein the lid is engageable with the dish to form a fluid tight compartment;

d. an outlet tube extending out of the lid, and adapted to direct the flushing solution out of the lid; and e. a sheet of filter material clamped between the dish and the lid, wherein the filter material is suspended over the unobstructed volume and is entirely unsupported inwardly of the dish and lid sidewalls, wherein the filter material allows the passage of the flushing solution from the dish to the lid, but retains the embryos within the dish, wherein the bottom may be placed on a microscope stage for viewing and extracting the animal embryos, wherein the dish sidewall is cylindrical, and the lid sidewall is cylindrical, wherein the dish is rotatably engaged with the lid, and the dish inlet tube is adapted to discharge into the dish through a dish discharge opening, wherein the lid outlet tube has a fluid outlet opening, and wherein the dish and lid are rotatable with respect to one another to position the outlet tube outlet opening with respect to a lowermost portion of the device to control the flushing solution level within the device.

2. A device for collecting animal embryos suspended in a flushing solution, the device comprising:

a. a dish having a bottom and an upwardly extending dish sidewall;

b. an inlet tube extending into the dish sidewall and adapted to direct flushing solution containing embryos into the dish;

c. a lid having a top and a downwardly extending sidewall, wherein the lid is engageable with the dish to form a fluid tight compartment, and wherein the lid has indicia thereon and the dish has spaced markings spaced peripherally around the dish sidewall, such that the lid may be angularly positioned with respect to the dish to set the volume of the flushing solution retained within the device;

d. an outlet tube extending out of the lid, and adapted to direct the flushing solution out of the lid;

e. a sheet of filter material clamped between the dish and the lid, wherein the filter material allows the passage of the flushing solution from the dish to the lid, but retains the embryos within the dish, and wherein the bottom may be placed on a microscope stage for viewing and extracting the animal embryos.

3. A device for collecting animal ova suspended in a flushing solution, the device comprising:
   a. a dish having a bottom and an upwardly extending cylindrical sidewall;
   b. an inlet tube extending into the dish sidewall and adapted to direct flushing solution containing ova into the dish;
   c. a lid having a top and a downwardly extending cylindrical sidewall, wherein the lid is rotatably engageable with the dish to form a fluid tight compartment;
   d. an outlet tube extending out of the lid, and adapted to direct the flushing solution out of the lid;
   e. a filter clamped between the dish and the lid, wherein the filter allows the passage of the flushing solution from the dish to the lid, but retains the ova within the dish, wherein the bottom may be placed on a microscope stage for viewing and extracting the animal ova, wherein the dish is rotatable with respect to the lid to adjust the relative vertical positioning of the outlet tube with respect to the inlet tube and to thus set the level of the flushing solution retained within the device, and wherein the lid is releasably connected to the dish entirely by a tight but releasable friction fit.

4. The device of claim 3 further comprising an annular retaining ting which surrounds the lid sidewall and clamps the filter to the lid, wherein the dish engages with the lid beneath the retaining ring.

5. A device for collecting animal ova suspended in a flushing solution, the device comprising:
   a. a dish having a bottom and an upwardly extending cylindrical sidewall;
   b. an inlet tube extending into the dish sidewall and adapted to direct flushing solution containing ova into the dish;
   c. a lid having a top and a downwardly extending cylindrical sidewall, wherein the lid is rotatably engageable with the dish to form a fluid tight compartment;
   d. an outlet tube extending out of the lid, and adapted to direct the flushing solution out of the lid;
   e. a filter clamped between the dish and the lid, wherein the filter allows the passage of the flushing solution from the dish to the lid, but retains the ova within the dish, wherein the bottom may be placed on a microscope stage for viewing and extracting the animal ova, wherein the dish is rotatable with respect to the lid to adjust the relative vertical positioning of the outlet tube with respect to the inlet tube and to thus set the level of the flushing solution retained within the device; and wherein the lid has indicia thereon and the dish has spaced markings spaced peripherally around the dish sidewall, such that the lid may be angularly positioned with respect to the dish to set the volume of the flushing solution retained within the device.

* * * * *